United States Patent

Miyauchi et al.

Patent Number: 5,807,696
Date of Patent: Sep. 15, 1998

[54] METHOD FOR DETERMINATION OF CHOLESTEROL IN LOW-DENSITY LIPOPROTEIN

[75] Inventors: Kazuhito Miyauchi; Akira Miike, both of Shizuoka, Japan

[73] Assignee: Kyowa Medex Co., Ltd., Tokyo, Japan

[21] Appl. No.: 737,504

[22] PCT Filed: Mar. 15, 1996

[86] PCT No.: PCT/JP96/00664

§ 371 Date: Nov. 13, 1996

§ 102(e) Date: Nov. 13, 1996

[87] PCT Pub. No.: WO96/28734

PCT Pub. Date: Sep. 19, 1996

[30] Foreign Application Priority Data

Mar. 16, 1995 [JP] Japan ................................ 7-57307

[51] Int. Cl.$^6$ ..................... C12Q 1/60; C12Q 1/00; C12Q 1/44; G01N 33/53

[52] U.S. Cl. ........................... 435/11; 435/4; 435/19; 435/25; 435/20; 435/975; 435/18; 436/71; 424/94.1; 424/94.4

[58] Field of Search .................... 435/11, 4, 19, 435/25, 20, 975, 18; 424/94.1, 94.4; 436/71

[56] References Cited

U.S. PATENT DOCUMENTS

| 4,275,151 | 6/1981 | Esders et al. | 435/11 |
| 4,544,630 | 10/1985 | Ziegenhorn et al. | 435/11 |
| 4,746,605 | 5/1988 | Kerscher et al. | 435/11 |
| 4,892,815 | 1/1990 | Kerscher et al. | 435/11 |
| 5,213,964 | 5/1993 | Jones | 435/11 |
| 5,286,626 | 2/1994 | Law et al. | 435/19 |

FOREIGN PATENT DOCUMENTS

| 0676642 | 10/1995 | European Pat. Off. . |
| 3262967 | 11/1991 | Japan . |

*Primary Examiner*—Louise N. Leary
*Attorney, Agent, or Firm*—Fitzpatrick, Cella, Harper & Scinto

[57] ABSTRACT

The present invention relates to a method for the determination of cholesterol in low-density lipoprotein (LDL) in a sample containing LDL, which comprises eliminating cholesterol in high-density lipoprotein in the sample, subjecting the sample to a reaction utilizing the action of a cholesterol ester-hydrolyzing enzyme and the action of a cholesterol-oxidizing enzyme or of cholesterol oxidoreductase, and determining the amount of hydrogen peroxide or a reduced type coenzyme generated by the reaction.

31 Claims, 3 Drawing Sheets

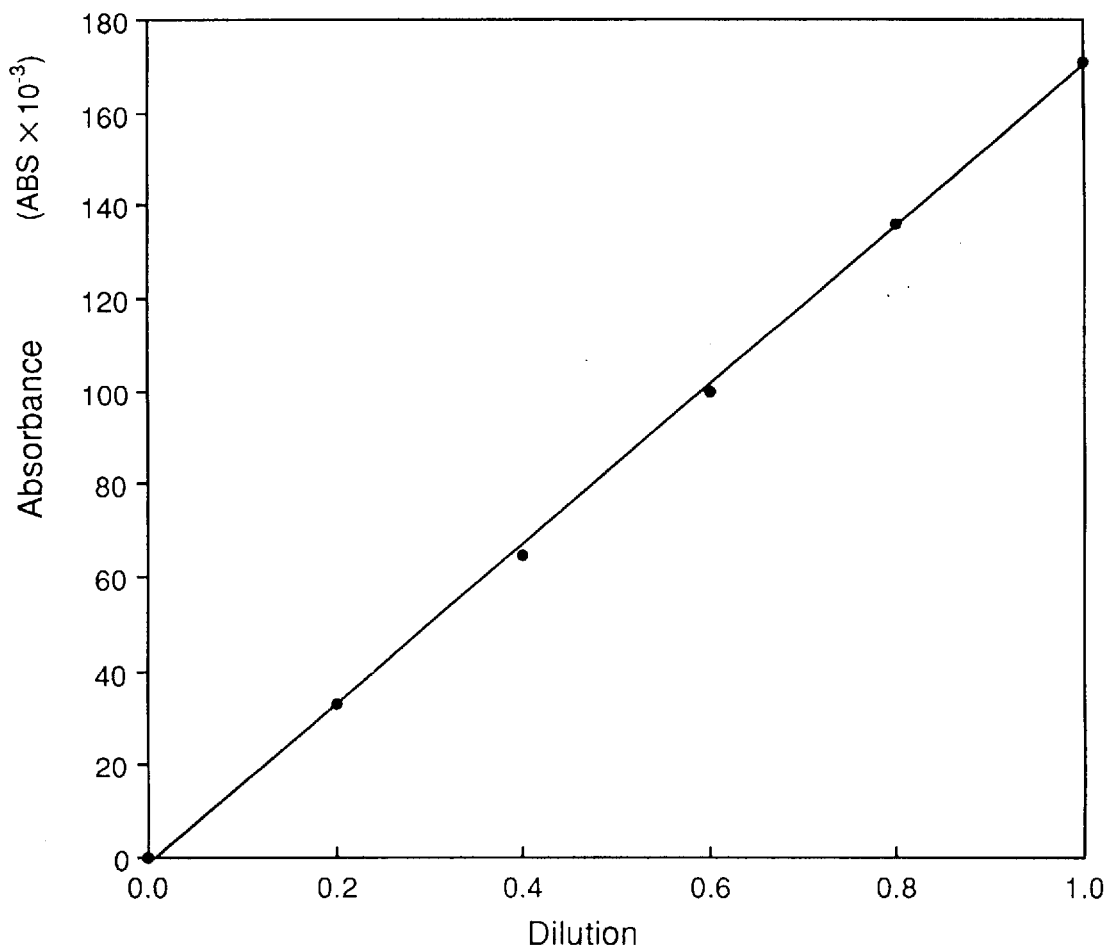

METHOD FOR DETERMINATION OF CHOLESTEROL IN LOW-DENSITY LIPOPROTEIN

TECHNICAL FIELD

The present invention relates to a method for the determination of cholesterol in low-density lipoprotein (LDL) (hereinafter referred to as LDL cholesterol) which is important for the diagnosis of arteriosclerosis in the field of clinical diagnosis.

BACKGROUND ART

The conventional method for the determination of LDL cholesterol comprises first determining the total amount of cholesterol in a portion of a given sample, then adding a precipitant for LDL and very low-density lipoprotein (VLDL) to a separate portion of the sample, centrifuging the resultant mixture to obtain a supernatant, determining the amount of cholesterol in high-density lipoprotein (HDL) (hereinafter referred to as HDL cholesterol) of the supernatant, and calculating the amount of LDL cholesterol in accordance with the Friedewald formula of conversion [Japanese Clinic (Nippon Rinsho), Extensive Chemical Test of Blood and Urine, Immunological Test, Volume 1, p. 615, published by Nippon Rinshosha, 1995]. This method requires determination of two quantities, i.e. the total amount of cholesterol and the amount of HDL cholesterol, and also requires the step of centrifugation, etc., which makes the process complicated. However, if a blood serum sample is directly added to a reagent containing cholesterol esterase and cholesterol oxidase, the resultant test system is not different from a system for the determination of total cholesterol and has no specificity to LDL cholesterol.

Japanese Published Unexamined Patent Application No. 165800/83 discloses a method for directly determining the amount of LDL cholesterol in the presence of a special surfactant without the step of separation. However, this method, which allows both of HDL cholesterol and LDL cholesterol to undergo the relevant reaction, has low LDL specificity and requires complicated setting of reaction conditions; thus it is not readily applicable to a variety of samples.

Japanese Published Unexamined Patent Application No. 280812/95 discloses a method which comprises aggregating LDL, eliminating cholesterol in lipoproteins other than LDL, resolving the LDL aggregation, and subjecting LDL cholesterol to an enzyme reaction to determine the amount of LDL cholesterol.

DISCLOSURE OF THE INVENTION

The present inventors have found a) that LDL cholesterol in a sample containing LDL can be specifically determined without particular separation thereof by specifically eliminating HDL cholesterol by a reaction with a reagent for the reaction of cholesterol in the presence of a reagent which inhibits the reaction of lipoproteins other than HDL, i.e. LDL, VLDL and chylomicron (CM), and then, if necessary in the presence of a reagent which enables the reaction of LDL cholesterol, subjecting LDL cholesterol to an enzyme reaction for the determination of cholesterol by the use of a reagent for the reaction of cholesterol, and b) that LDL cholesterol in a sample containing LDL can be specifically determined without particular separation thereof by inhibiting only the reaction of LDL, eliminating cholesterol in lipoproteins other than LDL by a reaction with a reagent for the reaction of cholesterol, and thereafter subjecting LDL cholesterol to an enzyme reaction for the determination of cholesterol by the use of a reagent for the reaction of cholesterol. The present invention has thus been completed.

The expression "inhibiting the reaction of lipoproteins other than HDL" as used herein means enabling selectively cholesterol in HDL to undergo an enzyme reaction by aggregating lipoproteins other than HDL or lowering the reactivity of the outer walls of lipoproteins other than HDL so as to render selectively unbreakable the outer walls of lipoproteins other than HDL. The expression "enabling the reaction of LDL cholesterol" means enabling LDL cholesterol to undergo an enzyme reaction by breaking the outer walls of LDL. The expression "inhibiting only the reaction of LDL" conversely means enabling selectively cholesterol in lipoproteins other than LDL to undergo an enzyme reaction by aggregating LDL or lowering the reactivity of the outer walls of LDL so as to render selectively unbreakable the outer walls of LDL.

The present invention relates to a method for the determination of LDL cholesterol in a sample containing LDL, which comprises eliminating HDL cholesterol in the sample, then subjecting the sample to a reaction utilizing the action of a cholesterol ester-hydrolyzing enzyme and the action of a cholesterol-oxidizing enzyme or of cholesterol oxidoreductase, if necessary in the presence of a reagent which enables the reaction of LDL cholesterol, and determining the amount of hydrogen peroxide or a reduced type coenzyme generated by the reaction.

The present invention also provides a reagent for the determination of cholesterol in LDL, which contains a reagent inhibiting the reaction of lipoproteins other than HDL and a reagent enabling the reaction of cholesterol in LDL; and a reagent for the determination of cholesterol in LDL, which is a kit composed of a reagent inhibiting the reaction of lipoproteins other than HDL and a reagent enabling the reaction of cholesterol in LDL.

Further, the present invention provides a reagent for the determination of cholesterol in LDL, which contains a reagent inhibiting only the reaction of LDL; a reagent for the determination of cholesterol in LDL, which contains a reagent inhibiting only the reaction of LDL and a reagent enabling the reaction of cholesterol in LDL; and a reagent for the determination of cholesterol in LDL, which is a kit composed of a reagent inhibiting only the reaction of LDL and a reagent enabling the reaction of cholesterol in LDL.

In accordance with the present invention, the determination of LDL cholesterol can be carried out as follows:

a) HDL cholesterol is specifically eliminated by a reaction with a reagent for the reaction of cholesterol in the presence of a reagent inhibiting the reaction of lipoproteins other than HDL, i.e. LDL, VLDL and CM, then, if necessary in the presence of a reagent enabling the reaction of LDL cholesterol, the sample is subjected to a reaction utilizing the action of a cholesterol ester-hydrolyzing enzyme and the action of a cholesterol-oxidizing enzyme or of cholesterol oxidoreductase, and the amount of hydrogen peroxide or a reduced type coenzyme generated by the reaction is determined; or b) cholesterol in lipoproteins other than LDL is eliminated by a reaction with a reagent for the reaction of cholesterol in the presence of a reagent inhibiting only the reaction of LDL, the sample is subjected to a reaction utilizing the action of a cholesterol ester-hydrolyzing enzyme and the action of a cholesterol-oxidizing enzyme or of cholesterol oxidoreductase, and the amount of hydrogen peroxide or a reduced type coenzyme generated by the reaction is determined.

For example, LDL cholesterol in a sample containing HDL and LDL can be determined by subjecting the sample to a reaction utilizing the action of a cholesterol ester-hydrolyzing enzyme and the action of a cholesterol-oxidizing enzyme in the presence of a reagent inhibiting the reaction of lipoproteins other than HDL to form hydrogen peroxide, subsequently or simultaneously adding catalase, peroxidase and an aniline compound, peroxidase and a phenol compound, or peroxidase and 4-aminoantipyrine to eliminate the hydrogen peroxide, and then adding a chromogen (in combination with peroxidase when catalase is used), and an appropriate surfactant, cyclodextrin, or a cholesterol ester-hydrolyzing enzyme capable of acting on LDL to the sample for color development. The expression "acting on LDL" as used herein means enabling LDL cholesterol to undergo an enzyme reaction by breaking the outer walls of LDL of which the reaction has been inhibited.

LDL cholesterol in a sample containing LDL can be determined by adding a cholesterol ester-hydrolyzing enzyme, a cholesterol-oxidizing enzyme, and a chromogen to the sample in the presence of a reagent inhibiting only the reaction of LDL to develop a color, and measuring the change in absorbance of the sample subsequent to the reaction of cholesterol in lipoproteins other than LDL.

LDL cholesterol in a sample containing LDL can also be determined by subjecting the sample to a reaction utilizing the action of a cholesterol ester-hydrolyzing enzyme and the action of a cholesterol-oxidizing enzyme in the presence of a reagent inhibiting only the reaction of LDL (which is not required when the cholesterol ester-hydrolyzing enzyme mentioned above inhibits only the reaction of LDL) to form hydrogen peroxide, subsequently or simultaneously adding catalase, peroxidase and an aniline compound, peroxidase and a phenol compound, or peroxidase and 4-aminoantipyrine to eliminate the hydrogen peroxide, and then adding a chromogen (in combination with peroxidase when catalase is used), and a reagent enabling the reaction of LDL cholesterol (which is not required when the cholesterol ester-hydrolyzing enzyme mentioned below enables the reaction of LDL cholesterol) and a cholesterol ester-hydrolyzing enzyme (which is not required when the initially added cholesterol ester-hydrolyzing enzyme is enabled to react with LDL cholesterol by the reagent enabling the reaction of LDL cholesterol) to the sample for color development.

The method of the present invention can be applied to body fluid samples containing LDL such as blood and urine.

Representative procedures for the determination according to the present invention are described below.

Procedure 1

The determination is carried out by (1) adding a neutral buffer solution containing a reagent inhibiting the reaction of lipoproteins other than HDL to a prescribed amount of a sample, followed by, for example, heating at 37° C. for several minutes, to inhibit the reaction of LDL, VLDL, and CM; (2) adding to the sample a cholesterol ester-hydrolyzing enzyme which is unreactive to LDL (preferably a chemically modified cholesterol ester-hydrolyzing enzyme), a cholesterol-oxidizing enzyme which is unreactive to LDL (preferably a chemically modified cholesterol-oxidizing enzyme) [or cholesterol oxidoreductase (preferably chemically modified cholesterol oxidoreductase) ], and catalase, peroxidase and an aniline compound, peroxidase and a phenol compound, or peroxidase and 4-aminoantipyrine [or NAD(P)] to eliminate HDL cholesterol by the reaction; (3) adding to the sample a surfactant, cyclodextrin, a chelating agent, a cholesterol ester-hydrolyzing enzyme capable of acting on LDL (preferably a chemically unmodified cholesterol ester-hydrolyzing enzyme), a cholesterol-oxidizing enzyme capable of acting on LDL (preferably a chemically unmodified cholesterol-oxidizing enzyme) or cholesterol oxidoreductase capable of acting on LDL (preferably chemically unmodified cholesterol oxidoreductase), and a chromogen [which is not added or replaced with NAD(P) when cholesterol oxidoreductase is used] for the reaction of LDL cholesterol to form hydrogen peroxide and to develop a color [or to form NAD(P)H]; and (4) measuring the absorbance of the formed pigment at the maximum wavelength with a spectrophotometer [measuring the increase of the NAD(P)H in terms of the absorbance at 300–500 nm, preferably 330–400 nm, for example at 340 nm, when cholesterol oxidoreductase is used (otherwise forming a formazan pigment by the addition of diaphorase and a tetrazolium salt, followed by colorimetric determination of the formazan pigment)]. The expression "being unreactive to LDL" as used herein means failing to break the outer walls of LDL to enable LDL cholesterol to undergo an enzyme reaction. The amount of LDL cholesterol is calculated on the basis of the absorbance separately determined by using a standard solution containing LDL cholesterol at a known concentration under the same conditions. Steps (1) and (2) may be carried out at the same time.

An example of the reagent inhibiting the reaction of lipoproteins other than HDL is a combination of an aggregating agent and a divalent metal salt. Examples of the aggregating agent are heparin and salts thereof, phosphotungstic acid and salts thereof, dextran sulfuric acid and salts thereof, polyethylene glycol, sulfated cyclodextrin and salts thereof, sulfated oligosaccharide and salts thereof, and mixtures thereof. Examples of the cyclodextrin are α-cyclodextrin, β-cyclodextrin, and γ-cyclodextrin. Examples of the oligosaccharide are maltotriose, maltotetraose, maltopentaose, maltohexaose, and maltoheptaose. Examples of the salt are sodium salt, potassium salt, lithium salt, ammonium salt, and magnesium salt. Examples of the divalent metal salt are magnesium salt, calcium salt, manganese salt, nickel salt, and cobalt salt.

Specifically, as the aggregating agent, 0.02–10 mM heparin having a molecular weight of 5,000–20,000 or a salt thereof, 0.1–10 mM phosphotungstic acid having a molecular weight of 4,000–8,000 or a salt thereof, 0.01–5 mM dextran sulfuric acid having a molecular weight of 10,000–500,000 or a salt thereof, 0.1–20 mM dextran sulfuric acid having a molecular weight of 1,000–10,000 or a salt thereof, 0.3–100 mM polyethylene glycol (PEG) having a molecular weight of 4,000–25,000, 0.1–50 mM sulfated cyclodextrin having a molecular weight of 1,000–3,000 or a salt thereof, 0.1–50 mM sulfated oligosaccharide having a molecular weight of 400–3,000 or a salt thereof, or any of the mixtures thereof is used. Preferably, 0.03–1 mM heparin having a molecular weight of 14,000–16,000 or a salt thereof, 0.1–3 mM phosphotungstic acid having a molecular weight of 5,000–7,000 or a salt thereof, 0.01–5 mM dextran sulfuric acid having a molecular weight of 150,000–250,000 or a salt thereof, 0.1–10 mM dextran sulfuric acid having a molecular weight of 1,000–5,000 or a salt thereof, 1.0–50 mM PEG having a molecular weight of 5,000–22,000, 0.1–10 mM sulfated cyclodextrin having a molecular weight of 1,000–2,000 or a salt thereof, 0.1–10 mM sulfated oligosaccharide having a molecular weight of 400–2,000 or a salt thereof, or any of the mixtures, thereof is used.

As the divalent metal salt, 0.1–50 mM magnesium salt, calcium salt, manganese salt, nickel salt, cobalt salt, etc. is used. Preferably, 0.1–50 mM magnesium salt is used.

As the reagent inhibiting the reaction of lipoproteins other than HDL, an antiapo-B antibody, an antiapo-C antibody, etc. may also be used. Examples of the antiapo-B antibody and antiapo-C antibody are: an IgG fraction which is obtained by immunizing rabbits against apoprotein B or apoprotein C purified from human blood serum, collecting antiapo-B antiserum or antiapo-C antiserum from the immunized rabbits, and subjecting the antiapo-B antiserum or antiapo-C antiserum to ammonium sulfate precipitation and salting out; and an antiapo-B monoclonal antibody or an antiapo-C monoclonal antibody which is obtained by immunizing mice against the apoprotein B or apoprotein C mentioned above [Introduction to Experimental Procedure for Monocloal Antibody, written by Tamie Ando, Kodansha Scientific, 21 (1991)].

As the enzymes, commercially available enzymes can be used. For example, cholesterol esterase and lipoprotein lipase derived from animals, plants or microorganisms having the ability to hydrolyze cholesterol ester, cholesterol oxidase derived from animals, plants or microorganisms having the ability to oxidize cholesterol to form hydrogen peroxide, and cholesterol dehydrogenase derived from animals, plants or microorganisms may be used. In order to improve the specificity and stability of these enzymes, they may be chemically modified with a group having polyethylene glycol as a main component, a group having polypropylene glycol as a main component, a group having a saccharide in the structure such as a water-soluble oligosaccharide residue, a sulfopropyl group, a polyurethane group, etc. Further, enzymes which are obtained by introduction of genes of the enzymes mentioned above into other microorganisms and subsequent expression thereof, optionally followed by chemical modification, and enzymes which are obtained by modification of genes of the enzymes mentioned above and subsequent expression thereof, optionally followed by chemical modification, can also be used.

Examples of the reagent for modifying the enzymes (chemical modifier) are compounds wherein polyethylene glycol and a group which can be bonded to an amino group are connected [e.g. Sunbright VFM4101 (NOF Corporation) wherein polyethylene glycol and a group which can be bonded to an amino group such as N-hydroxysuccinimido group are connected], Sunbright AKM series, ADM series, and ACM series [NOF Corporation: Chemical Engineering Monographs (Kagaku Kogaku Ronbunshu), 20 (3), 459 (1994)], which are compounds having the polyalkylene glycol structure and the acid anhydride structure, compounds wherein a copolymer of polyethylene glycol and polypropylene glycol and a group which can be bonded to an amino group are connected, copolymers of polyethylene glycol monomethacryl monomethyl ether and maleic anhydride, etc. Further, polyurethane P4000 activated (Boehringer Mannheim, Directions for Enzyme Modification Set) which is a chemical modifier for polyurethane, Dextran T40, TCT-activated (same as above) which is a chemical modifier for dextran, 1,3-propanesultone, etc. are also usable. By the use of these chemical modifiers, the enzymes can be modified with a group having polyethylene glycol as a main component, a group having polypropylene glycol as a main component, a group having a copolymer of polypropylene glycol and polyethylene glycol, a group having a saccharide in the structure, a sulfopropyl group, a polyurethane group, etc.

A method for the reaction of an enzyme with a chemical modifier is described below. It should be noted, however, that the method is not limited to this method. First, the enzyme is dissolved in a buffer such as HEPES buffer of pH 8 or above, and then, for example, Sunbright (0.01–500 times molar quantity of the enzyme) is added to the solution at 0°–50° C., followed by stirring for 5–60 minutes. The resulting reaction mixture is used as it is, or it is used after removal of low molecular weight compounds by ultrafiltration, if necessary. The cholesterol ester-hydrolyzing enzyme, cLolesterol-oxidizing enzyme, and cholesterol oxidoreductase are advantageously used at a concentration of 0.1–100 u/ml.

It is preferred that the cholesterol ester-hydrolyzing enzyme, cholesterol-oxidizing enzyme and cholesterol oxidoreductase which are unreactive to LDL be chemically modified with a group having polyethylene glycol as a main component, a group having polypropylene glycol as a main component, a group having a saccharide in the structure such as a water-soluble oligosaccharide residue, a sulfopropyl group, a polyurethane group, etc.

As the cholesterol ester-hydrolyzing enzyme, cholesterol-oxidizing enzyme and cholesterol oxidoreductase which are capable of acting on LDL, chemically unmodified enzymes are preferred. However, enzymes slightly modified for the sake of stabilization can be used insofar as they are capable of acting only on LDL. An example of the modifier to be used is Sunbright VFM4101 (NOF Corporation) mentioned above. The amount of the enzyme to be used is preferably 0.5–100 u/ml.

As the surfactant which is used for the purpose of rendering LDL reactive, nonionic surfactants such as Triton X-100, cationic surfactants and anionic surfactants are used in an amount of 0.02–20%. The cyclodextrin which is used for the purpose of rendering LDL reactive includes α-cyclodextrin, β-cyclodextrin, γ-cyclodextrin, dimethyl-α-cyclodextrin, dimethyl-β-cyclodextrin, dimethyl-γ-cyclodextrin, hydroxypropyl-α-cyclodextrin, hydroxypropyl-β-cyclodextrin, hydroxypropyl-γ-cyclodextrin, 2,3,6-O-methyl-β-cyclodextrin, and poly-β-cyclodextrin. The cyclodextrin is used in an amount of 0.1–10%. As the chelating agents which are used for the purpose of rendering LDL reactive, compounds which are capable of forming complexes with magnesium are advantageously used. For example, ethylenediaminetetraacetic acid (EDTA), triethylenetetramine-N,N,N',N",N"',N"'-hexaacetic acid (TTHA), and trans-1,2-cyclohexanediamine-N,N,N',N'-tetraacetic acid (CyDTA) monohydrate are used in an amount of 0.005–2%. As the chromogen which serves as a substrate for the cholesterol-oxidizing enzymes for the detection of hydrogen peroxide, combinations of 4-aminoantipyrine and Trinder's reagents [General Catalog of Dojin Kagaku Kenkyusho, 19th ed. (1994)] can be used, as well as generally employed combinations of 4-aminoantipyrine and phenols such as phenol, 4-chlorophenol, m-cresol and 3-hydroxy-2,4,6-triiodobenzoic acid (HTIB). Examples of the Trinder's reagent are anilines such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-3-sulfopropyl)-3,5-dimethoxyaniline (HDAOS), N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2- hydroxy-3-sulfopropyl)aniline and N-ethyl-N-(2-hydroxy-3-sulfopropyl)-3,5-dimethoxyaniline, N-ethyl-N-(3-methylphenyl)-N'-succinylethylenediamine (EMSE), and N-ethyl-N-(3-methylphenyl)-N'-acetylethylenediamine. As the chromogen of high sensitivity, 10-(N-methylcarbamoyl)-3,7-bis(dimethylamino)phenothiadine (MCDP) disclosed in Japanese Published Examined Patent Application No. 33479/85, bis[3-bis(4-chlorophenyl)methyl-4-dimethylaminophenyl]amine (BCMA) disclosed in Japanese Published Examined Patent Application No. 27839/92, the chromogens disclosed in Japanese Published Unexamined Patent Application No. 296/87, etc. can be used. These chromogens of high sensitivity may be used in combination with 4-aminoantipyrine or with the Trinder's reagents enumerated above. The concentration of the chromogen is preferably 0.01–10 mg/ml, and is limited by the solubility.

As the phenol compound and the aniline compound to be used in combination with peroxidase in the elimination of HDL, the phenols and the anilines enumerated above are similarly usable.

As the buffer, Tris buffer, Good's buffer, etc. are advantageously used as well as phosphate buffer. The concentration of the buffer is preferably 5–500 mM. The pH value thereof is preferably 5–9.

Procedure 2

The determination is carried out by (1) adding a sample to a buffer containing ascorbic acid oxidase, and adding to the resultant mixture a reagent containing a cholesterol ester-hydrolyzing enzyme having low reactivity to LDL (inhibiting only the reaction of LDL), a cholesterol-oxidizing enzyme having low reactivity to LDL (or cholesterol oxidoreductase having low reactivity to LDL), peroxidase and a chromogen [or NAD(P)]; and (2) subsequently to completion of the reaction of cholesterol in lipoproteins other than LDL, measuring the change in absorbance with a spectrophotometer, and calculating the amount of LDL cholesterol on the basis of the absorbance separately determined by using a standard solution containing LDL cholesterol at a known concentration under the same conditions.

As the cholesterol ester-hydrolyzing enzyme having low reactivity to LDL, a chemically modified cholesterol ester-hydrolyzing enzyme is preferably used. As the cholesterol-oxidizing enzyme or cholesterol oxidoreductase having low reactivity to LDL, a chemically modified or unmodified cholesterol-oxidizing enzyme or a chemically modified or unmodified cholesterol oxidoreductase can be used. An example of the modifier is Sunbright VFM4101 (NOF Corporation) mentioned above. The amount of the enzyme to be used is preferably 0.5–100 u/ml.

As the chromogen and the buffer, the chromogens and the buffers enumerated in Procedure 1 are similarly usable.

Procedure 3

The determination is carried out by (1) adding a sample to a buffer containing a reagent inhibiting only the reaction of LDL (which is not required when the cholesterol ester-hydrolyzing enzyme mentioned below inhibits only the reaction of LDL), a cholesterol ester-hydrolyzing enzyme, a cholesterol-oxidizing enzyme (or cholesterol oxidoreductase), and catalase, peroxidase and an aniline compound, peroxidase and a phenol compound, or peroxidase and 4-aminoantipyrine [or NAD(P)] to eliminate cholesterol in lipoproteins other than LDL by the reaction; (2) adding a reagent enabling the reaction of LDL cholesterol (which is not required when the cholesterol ester-hydrolyzing enzyme mentioned below enables the reaction of LDL cholesterol), a cholesterol ester-hydrolyzing enzyme (which is not required when the initially added cholesterol ester-hydrolyzing enzyme is enabled to react with LDL cholesterol by the reagent enabling the reaction of LDL cholesterol), and a chromogen [which may be unnecessary or replaced with NAD(P)] (in combination with peroxidase when catalase is used) for the reaction of LDL cholesterol to form hydrogen peroxide and to develop a color [or to form NAD(P)H]; and (3) measuring the absorbance of the formed pigment at the maximum wavelength with a spectrophotometer [measuring the increase of NAD(P)H in terms of the absorbance at 300–500 nm, preferably 330–400 nm, for example at 340 nm when cholesterol oxidoreductase is used (otherwise forming a formazan pigment by the addition of diaphorase and a tetrazolium salt, followed by calorimetric determination of the formazan pigment)]. The amount of LDL cholesterol is calculated on the basis of the absorbance separately determined by using a standard solution containing LDL cholesterol at a known concentration under the same conditions.

As the reagent inhibiting only the reaction of LDL, a cholesterol ester-hydrolyzing enzyme capable of inhibiting only the reaction of LDL etc. can be used. As the reagent enabling the reaction of LDL cholesterol, a cholesterol ester-hydrolyzing enzyme enabling the reaction of LDL cholesterol, a surfactant, a chelating agent, etc. can be used.

As the surfactant and the chelating agent, the surfactants and the chelating agents enumerated in Procedure 1 are similarly usable.

As the enzymes, the enzymes enumerated in Procedure 1 are similarly usable.

As the cholesterol ester-hydrolyzing enzyme capable of inhibiting only the reaction of LDL, a cholesterol ester-hydrolyzing enzyme prepared by adding to a cholesterol ester-hydrolyzing enzyme derived from an animal, a plant or a microorganism a chemical modifier (not less than 10 times molar quantity of the enzyme), and a cholesterol ester-hydrolyzing enzyme derived from an animal, a plant or a microorganism which has similar specifity, or which is endowed with similar specificity by modification of genes of the enzymes mentioned above and subsequent expression thereof, can be preferably used. Specifically, the product of the reaction of cholesterol esterase derived from a microorganism belonging to the genus Pseudomonas, Chromobacterium, etc. in an aqueous solution with the chemical modifier mentioned in Procedure 1 (not less than 10 times molar quantity of the enzyme) may be cited as an example. The molar ratio of the chemical modifier to the enzyme is preferably 10–500:1 and is determined considering the effect of endowing specificity and the degradation of activity by the modification. As the chemically unmodified cholesterol ester-hydrolyzing enzyme, for example, an enzyme obtained by the following steps can be used: randomly altering a part of the DNA sequence of lipase derived from a microorganism belonging to the genus Brevibacterium, introducing the altered gene into other microorganism such as *E. coli,* allowing it to be expressed therein, selecting by screening a strain which produces cholesterol esterase exhibiting the enzymatic activity and possessing the ability to inhibit only the reaction of LDL, and mass culturing the strain. The cholesterol ester-hydrolyzing enzyme is advantageously used at a concentration of 0.1–100 u/ml. For the purpose of enhancing the specificity mentioned above, heparin, phosphotungstic acid, dextran sulfuric acid, sulfated cyclodextrin, sulfated oligosaccharide, or a salt thereof, or polyethylene glycol may be added together with a divalent metal salt such as magnesium salt, calcium salt, manganese salt, nickel salt and cobalt salt during the step of (1) mentioned above in an amount not so large as to induce aggregation of LDL. As the cyclodextrin, oligosaccharide, and salt, the cyclodextrins, oligosaccharides, and salts enumerated in Procedure 1 are similarly usable.

As the cholesterol ester-hydrolyzing enzyme enabling the reaction of LDL cholesterol, unmodified cholesterol esterase is preferred. It is preferable to use the enzyme at a concentration of 0.5–100 u/ml.

As the cholesterol-oxidizing enzyme or cholesterol oxidoreductase, cholesterol oxidase derived from microorganisms having the ability of oxidizing cholesterol to form hydrogen peroxide, and cholesterol dehydrogenase derived from an animal or a microorganism are advantageously used. The enzymes mentioned above may be chemically modified with a group having polyethylene glycol as a main component or a water-soluble oligosaccharide residue for the purpose of enhancing the specificity and stability thereof. The molar ratio of the chemical modifier to the enzyme is preferably 0.1–500:1 and is determined considering the effect of stabilization and the degradation of activity by the modification. The cholesterol-oxidizing enzyme and cholesterol oxidoreductase are advantageously used at a concentration of 0.1–100 u/ml.

A method for the reaction of an enzyme with a chemical modifier is described below. It should be noted, however, that the method is not limited to this method. First, the enzyme is dissolved in a buffer such as HEPES buffer of pH 8 or above, and then a prescribed molar quantity of Sunbright is added to the solution at 0°–50° C., followed by stirring for 1–24 hours. The resulting reaction mixture is used as it is, or it is used after removal of low molecular weight compounds by ultrafiltration, if necessary.

As the phenol compound and the aniline compound to be used in combination with peroxidase in the elimination of cholesterol in lipoproteins other than LDL, the phenols and the anilines enumerated above are similarly usable. As the chromogen and the buffer, the chromogens and the buffers enumerated above are similarly usable.

Since the systems of the present invention described above each includes an ordinary system for the determination of cholesterol, a surfactant or cholic acid which is often used to activate a cholesterol-oxidizing enzyme can also be employed. Further, various salts for solubilizing proteins such as globulin may be used. As the surfactant, nonionic, anionic, and cationic surfactants are used in an amount of 0–1%. Examples of the cholic acid are cholic acid, deoxycholic acid, taurocholic acid, and chenodeoxycholic acid. The cholic acid is used in an amount of 0–5%. Examples of the salt are sodium chloride, sodium sulfate, potassium chloride, potassium sulfate, magnesium chloride, magnesium sulfate, magnesium acetate, magnesium nitrate, lithium chloride, lithium sulfate, ammonium chloride, ammonium sulfate, calcium chloride, calcium nitrate, calcium acetate, nickel chloride, nickel nitrate, nickel acetate, cobalt chloride, and (cobalt nitrate. The salt is used at a concentration of 0–100 mM.

BRIEF DESCRIPTION OF THE DRAWINGS

FIG. 3 is a graph showing the correlation between the dilution of blood serum containing 228.4 mg/dl LDL cholesterol and the absorbance as determined by the method of Example 11.

Examples of the present invention are shown below.

BEST MODE FOR CARRYING OUT THE INVENTION

Example 1 Determination of LDL cholesterol
(1) Chemical modification of enzyme

Cholesterol esterase derived from a microorganism belonging to the genus Pseudomonas (1 g) was dissolved in 100 ml of a 20 mM phosphate buffer (pH 8), followed by cooling to 5° C. To the solution was added 15 g of Sunbright VFM4101 (NOF Corporation), and the mixture was subjected to reaction for 4 hours. The resulting reaction mixture was used as the PEG-modified cholesterol esterase in Reagent B (molecular weight of PEG moiety=6000). Separately, 1 g of cholesterol oxidase derived from a microorganism belonging to the genus Brevibacterium and 0.1 g of Sunbright VFM4101 were subjected to reaction in the same manner as above. The resulting reaction mixture was used as the PEG-modified cholesterol oxidase in Reagent B (molecular weight of PEG moiety=6000).

(2) Determination of LDL cholesterol

| Reagent A | 3-Morpholinopropane sulfonic acid (MOPS) buffer | 20 mM (pH 7) |
|---|---|---|
| | Dextran sulfuric acid | 0.7 g/l |
| | Mg sulfate heptahydrate | 7.5 g/l |
| | Sodium azide | 0.1 g/l |
| | Ascorbic acid oxidase | 3 u/ml |
| Reagent B | MOPS buffer | 20 mM (pH 7) |
| | Peroxidase | 30 u/ml |
| | PEG-modified cholesterol esterase | 1 u/ml |
| | PEG-modified cholesterol oxidase | 3 u/ml |
| | Sodium cholate | 5 g/l |
| | EMSE | 0.3 g/l |
| Reagent C | MOPS buffer | 20 mM (pH 7) |
| | Unmodified cholesterol esterase | 2 u/ml |
| | 4-Aminoantipyrine | 0.4 g/l |

The following samples were used: (1) a blood serum containing 228.4 mg/dl LDL cholesterol, (2) a 8:10 dilution of the serum of (1) with physiological saline, (3) a 6:10 dilution of the serum of (1) with physiological saline, (4) a 4:10 dilution of the serum of (1) with physiological saline, (5) a 2:10 dilution of the serum of (1) with physiological saline, and (6) physiological saline.

To 2.25 ml of Reagent A was added 20 μl of a sample, and the mixture was incubated at 37° C. for 5 minutes. Then, 0.75 ml of Reagent B was added thereto and the mixture was incubated at 37° C. for 5 minutes to eliminate HDL cholesterol, and the absorbance (E1) was measured at 555 nm. After addition of 0.75 ml of Reagent C, the mixture was further incubated at 37° C. for 5 minutes, and the absorbance (E2) was measured at a wavelength of 555 nm. The concentration of LDL cholesterol was calculated by separately subjecting a standard solution of cholesterol at a concentration of 200 mg/dl to the same procedure and comparing the respective values of (E2−E1)×dilution ratio. The term "dilution ratio" used herein means the volume ratio of (Reagent A+Reagent B)/(Reagent A+Reagent B+Reagent C).

Figure 1:
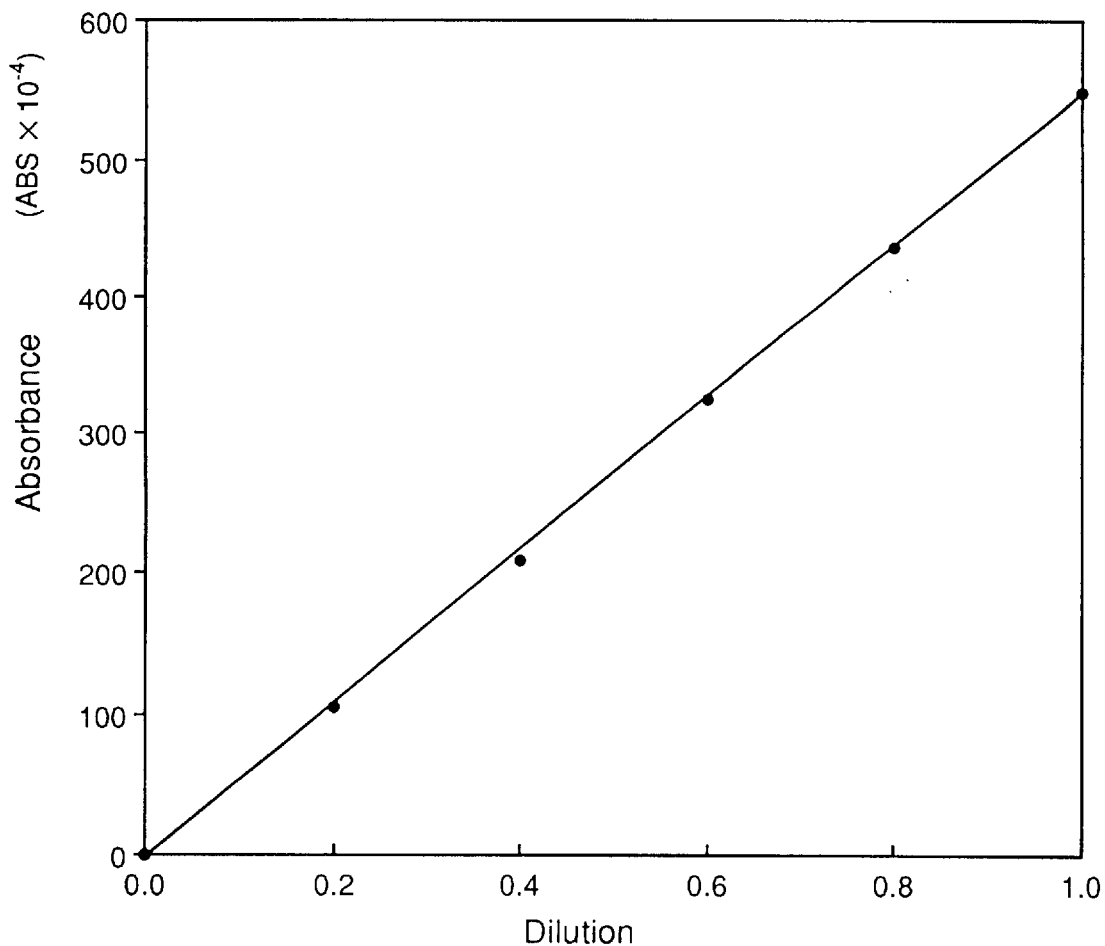
FIG. 1 is a graph showing the correlation between the dilution of blood serum containing 228.4 mg/dl LDL cholesterol and the absorbance as determined by the method of Example 1.

The results obtained by using the blood serum containing 228.4 mg/dl LDL cholesterol are shown in FIG. 1.

Example 2

Blood serum samples were subjected to the determination of LDL cholesterol using Reagent B and Reagent C described in Example 1 (2) and the combinations of an aggregating agent and a divalent metal salt shown below in Reagent A with an autoanalyzer (Hitachi 7070) (4 μl of sample, 270 μl of Reagent A, 90 μl of Reagent B, and 90 μl of Reagent C). Separately, the sample was subjected to the determination of LDL cholesterol in accordance with the method described in "Igaku no Ayumi", 94 (8), 359 (1975) (ultracentifugation method) using a rotor (Hitachi RPL 42 T). As apparent from Table 1, the results obtained by using Reagents A, B and C showed good agreement with the result obtained by the ultracentrifugation method.

| <A> | Phosphotungstic acid | 10 mg/ml |
| | Mg sulfate heptahydrate | 7.5 mg/ml |
| <B> | Sodium dextran sulfate (MW: 4000) | 1 mg/ml |
| | Mg sulfate heptahydrate | 10 mg/ml |
| <C> | Heparin sodium salt | 10 mg/ml |
| | Ca chloride dihydrate | 10 mg/ml |
| <D> | PEG 20000 | 50 mg/ml |
| | Mg sulfate heptahydrate | 5 mg/ml |
| <E> | Phosphotungstic acid | 10 mg/ml |
| | Sodium dextran sulfate (MW: 200000) | 7.5 mg/ml |
| | Mg sulfate heptahydrate | 7.5 mg/ml |
| <F> | Phosphotungstic acid | 10 mg/ml |
| | Heparin sodium salt | 7.5 mg/ml |
| | Mg sulfate heptahydrate | 7.5 mg/ml |
| <G> | Phosphotungstic acid | 10 mg/ml |
| | PEG 6000 | 7.5 mg/ml |
| | Mg sulfate heptahydrate | 7.5 mg/ml |

TABLE 1

| Reagent A | Value found |
|---|---|
| <A> | 177.7 mg/dl |
| <B> | 178.9 mg/dl |
| <C> | 178.1 mg/dl |
| <D> | 177.2 mg/dl |
| <E> | 179.0 mg/dl |
| <F> | 178.8 mg/dl |
| <G> | 176.5 mg/dl |
| Ultracentrifugation method | 178.4 mg/dl |

Example 3

Chemical modification of the enzymes was carried out by the same procedure as in Example 1 (1) except that Sunbright AKM1511 (NOF Corporation), polyurethane P4000 activated (Boehringer Mannheim), and Dextran T40, TCT-activated (Boehringer Mannheim) were respectively used in place of Sunbright VFM4101. The same blood serum samples as used in Example 2 were subjected to the determination of LDL cholesterol in a similar manner as in Example 2 using Reagent A and Reagent C described in Example 1 (2) and using the chemically modified enzymes obtained above in place of the PEG-modified cholesterol esterase and the PEG-modified cholesterol oxidase in Reagent B. The concentration of LDL cholesterol were determined to be 178.0 mg/dl, 179.1 mg/dl, and 179.8 mg/dl, respectively, which showed good agreement with the result obtained by the ultracentrifugation method.

Example 4

The same blood serum sample as used in Example 2 was subjected to the determination of LDL cholesterol in a similar manner as in Example 2 using Reagent A described in Example 1 (2), using catalase at a concentration of 300 u/ml in place of peroxidase in Reagent B, and using additionally peroxidase at a concentration of 30 u/ml in Reagent C. The concentration of LDL cholesterol was determined to be 178.6 mg/dl, which showed good agreement with the result obtained by the ultracentrifugation method.

Example 5

The same blood serum samples as used in Example 2 were subjected to the determination of LDL cholesterol in a similar manner as in Example 2 using Reagent A and Reagent C described in Example 1 (2) and using TOOS (measurement at 555 nm), DAOS (measurement at 593 nm), MAOS (measurement at 630 nm), and TOPS (measurement at 550 nm), respectively, at a concentration of 0.3 g/l in place of EMSE in Reagent B. The concentrations of LDL cholesterol were determined to be 177.9 mg/dl, 177.8 mg/dl, 179.2 mg/dl, and 178.8 mg/dl, respectively, which showed good agreement with the result obtained by the ultracentrifugation method.

Example 6

The same blood serum samples as used in Example 2 were subjected to the determination of LDL cholesterol in a similar manner as in Example 2 using Reagent A and Reagent B described in Example 1 (2) and using MCDP (measurement at 666 nm) and BCMA (measurement at 755 nm), respectively, at a concentration of 0.1 mg/ml in place of 4-aminoantipyrine in Reagent C. The concentrations of LDL cholesterol were determined to be 178.3 mg/dl and 179.0 mg/dl, respectively, which showed good agreement with the result obtained by the ultracentrifugation method.

Example 7

The same blood serum sample as used in Example 2 was subjected to the determination of LDL cholesterol in a similar manner as in Example 2 using Reagent A and Reagent B described in Example 1 (2) and using dimethyl-β-cyclodextrin at a concentration of 20 mg/ml in place of the unmodified cholesterol esterase in Reagent C. The concentration of LDL cholesterol was determined to be 177.4 mg/dl, which showed good agreement with the result obtained by the ultracentrifugation method.

Example 8

Reagent A and Reagent B described in Example 1 (2) were mixed at a ratio of 3:1 to prepare Reagent D. To 3 ml of Reagent D was added 20 μl of the same blood serum sample as used in Example 2, and after incubation at 37° C. for 5 minutes, the absorbance (E1) was measured at 555 nm. After addition of 0.75 ml of Reagent C, the mixture was further incubated at 37° C. for 5 minutes, and the absorbance (E2) was measured at a wavelength of 555 nm. The concentration of LDL cholesterol was calculated by separately subjecting a standard solution of cholesterol at a concentration of 200 mg/dl to the same procedure and comparing the respective values of (E2−E1)×dilution ratio. The term "dilution ratio" used herein means the volume ratio of (Reagent D)/(Reagent D+Reagent C). The concentration of LDL cholesterol was determined to be 177.6 mg/dl, which showed good agreement with the result obtained by the ultracentrifugation method.

Example 9

| Reagent A | MOPS buffer | 10 mM (pH 7) |
| | Na sulfate | 2 mg/ml |
| | EMSE | 0.3 mg/ml |
| | Ascorbic acid oxidase | 3 u/ml |
| Reagent B | MOPS buffer | 10 mM (pH 7) |
| | 4-Aminoantipyrine | 0.5 mg/ml |
| | Sodium cholate | 3 mg/ml |
| | PEG-modified cholesterol esterase | 5 u/ml |
| | Unmodified cholesterol oxidase | 7 u/ml |
| | Peroxidase | 10 u/ml |

The same PEG-modified cholesterol esterase as used in Example 1 was used in this Example.

The same blood serum sample as used in Example 2 was subjected to the determination of LDL cholesterol with an autoanalyzer (Hitachi 7250) using the reagents mentioned above. The change of absorbance (E3) between 3.5 minutes and 5 minutes after the addition of Reagent B was measured. The concentration of LDL cholesterol was calculated by separately subjecting a standard solution of cholesterol at a concentration of 200 mg/dl to the same procedure to measure the change of absorbance (E4) and comparing the values of E3 and E4. The concentration of LDL cholesterol was determined to be 178.6 mg/dl, which showed good agreement with the result obtained by the ultracentrifugation method.

Figure 2:
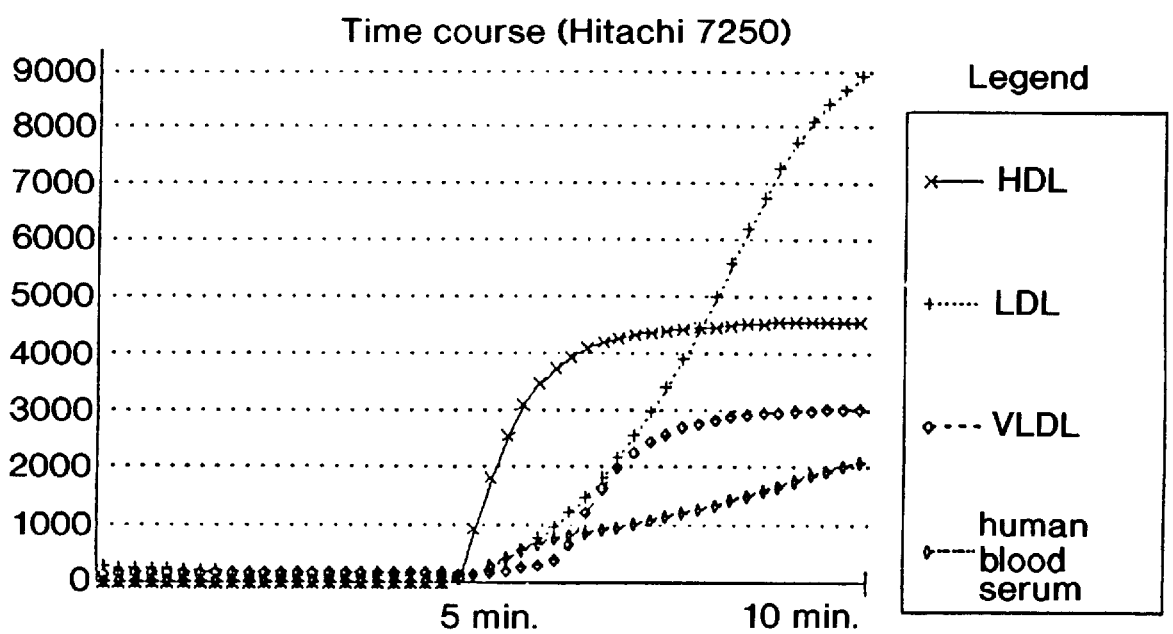
FIG. 2 is a graph showing the time course of the absorbance as determined with an autoanalyzer (Hitachi 7250) by the method of Example 9 using HDL, LDL and VLDL separated by ultracentrifugation method and human blood serum.

FIG. 2 shows the time course of the absorbance as determined using HDL, LDL and VLDL separated by the ultracentrifugation method and human blood serum.

Example 10

| Reagent A | MOPS buffer | 10 mM (pH 7) |
|---|---|---|
| | Sodium dextran sulfate (MW: 500000) | 0.5 mg/ml |
| | Mg sulfate heptahydrate | 5 mg/ml |
| | EMSE | 0.3 mg/ml |
| | Peroxidase | 10 u/ml |
| | PEG-modified cholesterol esterase | 2 u/ml |
| | Unmodified cholesterol oxidase | 3 u/ml |
| | Ascorbic acid oxidase | 3 u/ml |
| Reagent B | MOPS buffer | 10 mM (pH 7) |
| | 4-Aminoantipyrine | 0.5 mg/ml |
| | Triton X-100 | 3 mg/ml |
| | EDTA tetrasodium salt | 5 u/ml |

The same PEG-modified cholesterol esterase as used in Example 1 was used in this Example.

The same blood serum sample as used in Example 2 was subjected to the determination of LDL cholesterol with an autoanalyzer (Hitachi 7250) using the reagents mentioned above (absorbance: E5). The concentration of LDL cholesterol was calculated by separately subjecting a standard solution of cholesterol at a concentration of 200 mg/dl to the same procedure (absorbance: E6) and comparing the values of E5 and E6. The concentration of LDL cholesterol was determined to be 177.3 mg/dl, which showed good agreement with the result obtained by the ultracentrifugation method. The absorbance measurements with the autoanalyzer were made 5 minutes after the addition of Reagent B.

Example 11

(1) Chemical modification of enzyme

Cholesterol esterase derived from a microorganism belonging to the genus Pseudomonas (1 g) was dissolved in 100 ml of a 20 mM phosphate buffer (pH 8), followed by cooling to 15° C. To the solution was added 25 g of Sunbright VFM4101 (NOF Corporation), and the mixture was subjected to reaction for 4 hours. The resulting reaction mixture was used as the PEG-modified cholesterol esterase in Reagent B (molecular weight of PEG moiety=6000). Separately, 1 g of cholesterol oxidase derived from a microorganism belonging to the genus Brevibacterium and 0.5 g of Sunbright VFM4101 were subjected to reaction in the same manner as above. The resulting reaction mixture was used as the PEG-modified cholesterol oxidase in Reagent A (molecular weight of PEG moiety=6000).

(2) Determination of LDL cholesterol

| Reagent A | MOPS buffer | 20 mM (pH 7) |
|---|---|---|
| | Mg sulfate heptahydrate | 2 g/l |
| | Peroxidase | 30 u/ml |
| | PEG-modified cholesterol esterase | 2 u/ml |
| | PEG-modified cholesterol oxidase | 5 u/ml |
| | Sodium cholate | 1 g/l |
| | EMSE | 0.3 g/l |
| | Ascorbic acid oxidase | 3 u/ml |
| Reagent B | MOPS buffer | 20 mM (pH 7) |
| | Unmodified cholesterol esterase | 3 u/ml |
| | 4-Aminoantipyrine | 0.4 g/l |

The following samples were used: (1) a blood serum containing 228.4 mg/dl LDL cholesterol as determined by the ultracentrifugation method, (2) a 8:10 dilution of the serum of (1) with physiological saline, (3) a 6:10 dilution of the serum of (1) with physiological saline, (4) a 4:10 dilution of the serum of (1) with physiological saline, (5) a 2:10 dilution of the serum of (1) with physiological saline, and (6) physiological saline.

To 2.25 ml of Reagent A was added 20 μl of a sample, and the mixture was incubated at 37° C. for 5 minutes to eliminate cholesterol in lipoproteins other than LDL. After addition of 0.75 ml of Reagent B, the mixture was further incubated at 37° C. for 5 minutes, and the absorbance was measured at a wavelength of 600 nm. The results are shown in FIG. 3.

Separately, to a 3:1 mixture of Reagent A and Reagent B was added 20 μl of a standard solution of cholesterol at a concentration of 200 mg/dl, the mixture was incubated at 37° C. for 5 minutes, and the absorbance was measured at a wavelength of 600 nm. The concentration of LDL cholesterol in the blood serum sample mentioned above was calculated based on the absorbance thus obtained. The concentration of LDL cholesterol was determined to be 229.7 mg/dl, which showed good agreement with the result obtained by the ultracentrifugation method.

Example 12

The same blood serum samples as used in Example 11 (2) were subjected to the determination of LDL cholesterol using Reagent B described in Example 11 (2) and using additionally the combinations of an aggregating agent and a divalent metal salt shown below in Reagent A with an autoanalyzer (Hitachi 7070) (4 μl of sample, 270 μl of Reagent A, and 90 μl of Reagent B). Separately, the sample was subjected to the determination of LDL cholesterol in accordance with the method described in Modern Medical Treatment (Gendai Iryo), 23 (1), 113 (1991) (ultracentrifugation method) using a rotor (Hitachi RPL 42 T). As apparent from Table 2, the results obtained by using Reagents A and B showed good agreement with the result obtained by the ultracentrifugation method.

| <A> | Phosphotungstic acid | 0.1 mg/ml |
|---|---|---|
| | Mg sulfate heptahydrate | 1 mg/ml |
| <B> | Sodium dextran sulfate (MW: 20000) | 0.1 mg/ml |
| | Mg sulfate heptahydrate | 2 mg/ml |
| <C> | Heparin sodium salt | 0.3 mg/ml |
| | Ca chloride dihydrate | 3 mg/ml |
| <D> | PEG 20000 | 20 mg/ml |
| | Mg sulfate heptahydrate | 3 mg/ml |
| <E> | Phosphotungstic acid | 0.1 mg/ml |
| | Sodium dextran sulfate (MW: 200000) | 0.1 mg/ml |

-continued

| | | |
|---|---|---|
| | Mg sulfate heptahydrate | 2 mg/ml |
| <F> | Phosphotungstic acid | 0.1 mg/ml |
| | Heparin sodium salt | 0.1 mg/ml |
| | Mg sulfate heptahydrate | 2 mg/ml |
| <G> | Dextran sulfuric acid (MW: 500000) | 0.1 mg/ml |
| | PEG 6000 | 5 mg/ml |
| | Mg sulfate heptahydrate | 2 mg/ml |

TABLE 2

| Reagent A | Value found |
|---|---|
| <A> | 224.5 mg/dl |
| <B> | 229.1 mg/dl |
| <C> | 226.6 mg/dl |
| <D> | 227.3 mg/dl |
| <E> | 227.0 mg/dl |
| <F> | 230.8 mg/dl |
| <G> | 225.9 mg/dl |
| Ultracentrifugation method | 228.4 mg/dl |

Example 13

Chemical modification of the enzymes was carried out by the same procedure as in Example 11 (1) except that Sunbright AKM1511 (NOF Corporation), polyurethane P4000 activated (Boehringer Mannheim), and Dextran T40, TCT-activated (Boehringer Mannheim) were respectively used in place of Sunbright VFM4101. The same blood serum samples as used in Example 11 (2) were subjected to the determination of LDL cholesterol in a similar manner as in Example 11 (2) using Reagent B described in Example 11 (2) and using the chemically modified enzymes obtained above in place of the PEG-modified cholesterol esterase and the PEG-modified cholesterol oxidase in Reagent A. The concentrations of LDL cholesterol were determined to be 228.0 mg/dl, 229.1 mg/dl, and 226.8 mg/dl, respectively, which showed good agreement with the result obtained by the ultracentrifugation method.

Example 14

The same blood serum sample as used in Example 11 (2) was subjected to the determination of LDL cholesterol in a similar manner as in Example 11 (2) using catalase at a concentration of 300 u/ml in place of peroxidase in Reagent A described in Example 11 (2) and using additionally 300 u/ml peroxidase and 0.5 mg/ml sodium azide in Reagent B. The concentration of LDL cholesterol was determined to be 228.6 mg/dl, which showed good agreement with the result obtained by the ultracentrifugation method.

Example 15

The same blood serum samples as used in Example 11 (2) were subjected to the determination of LDL cholesterol in a similar manner as in Example 11 (2) using Reagent B described in Example 11 (2) and using TOOS (measurement at 555 nm), DAOS (measurement at 593 nm), MAOS (measurement at 630 nm), and TOPS (measurement at 550 nm), respectively, at a concentration of 0.3 g/l in place of EMSE in Reagent A. The concentrations of LDL cholesterol were determined to be 227.9 mg/dl, 227.4 mg/dl, 225.2 mg/dl, and 224.8 mg/dl, respectively, which showed good agreement with the result obtained by the ultracentrifugation method.

Example 16

The same blood serum samples as used in Example 11 (2) were subjected to the determination of LDL cholesterol in a similar manner as in Example 11 (2) using Reagent A free of EMSE and using MCDP (measurement at 666 nm) and BCMA sulfate (measurement at 755 nm), respectively, at a concentration of 0.1 mg/ml in place of 4-aminoantipyrine in Reagent B. The concentrations of LDL cholesterol were determined to be 228.3 mg/dl and 229.0 mg/dl, respectively, which showed good agreement with the result obtained by the ultracentrifugation method.

Example 17

The same blood serum samples as used in Example 11 (2) were subjected to the determination of LDL cholesterol in a similar manner as in Example 11 (2) using Reagent A described in Example 11 (2) and using additionally 5 mg/ml polyoxyethylene monolaurate, 5 mg/ml Triton X-100, and 1 mg/ml sodium dodecylbenzenesulfonate, respectively, in Reagent B. The reactions were completed within 3 minutes. The concentrations of LDL cholesterol were determined to be 228.6 mg/dl, 226.1 mg/dl, and 227.0 mg/dl, respectively, which showed good agreement with the result obtained by the ultracentrifugation method.

Example 18

The same blood serum samples as used in Example 11 (2) were subjected to the determination of LDL cholesterol in a similar manner as in Example 11 (2) using Reagent A described in Example 11 (2) and using 5 mg/ml polyoxyethylene monolaurate, 5 mg/ml Triton X-100, and 1 mg/ml sodium dodecylbenzenesulfonate, respectively, in place of the unmodified cholesterol esterase in Reagent B. The reactions were completed within 3 minutes. The concentrations of LDL cholesterol were determined to be 227.9 mg/dl, 229.2 mg/dl, and 226.1 mg/dl, respectively, which showed good agreement with the result obtained by the ultracentrifugation method.

Example 19

The same blood serum samples as used in Example 11 (2) were subjected to the determination of LDL cholesterol in a similar manner as in Example 11 (2) using Reagent B described in Example 11 (2) and using deoxycholic acid and taurocholic acid, respectively, at a concentration of 1 g/l in place of cholic acid in Reagent A. The concentrations of LDL cholesterol were determined to be 229.9 mg/dl and 225.7 mg/dl, respectively, which showed good agreement with the result obtained by the ultracentrifugation method.

Industrial Applicability

The present invention provides a simple method for the determination of LEL cholesterol which does not require complicated separation steps.

We claim:

1. A method for the determination of cholesterol in low-density lipoprotein (LDL) in a sample containing LDL which comprises:

reacting cholesterol in high-density lipoprotein (HDL) in the sample with a reagent for the reaction of cholesterol in the presence of a reagent inhibiting the reaction of LDL, subjecting the sample to a reaction utilizing the action of a cholesterol ester-hydrolyzing enzyme and the action of a cholesterol-oxidizing enzyme or of cholesterol oxidoreductase, determining an amount of hydrogen peroxide or a reduced type coenzyme generated by the reaction, and correlating the amount of hydrogen peroxide or a reduced type coenzyme with the quantity of cholesterol in LDL in said sample, wherein said method occurs without separating HDL cholesterol from said sample.

2. The method according to claim 1, wherein the reaction utilizing the action of a cholesterol ester-hydrolyzing enzyme and the action of a cholesterol-oxidizing enzyme or of cholesterol oxidoreductase is carried out in the presence of a reagent which enables the reaction of cholesterol in LDL.

3. The method according to claim 2, wherein the reaction for elimination of cholesterol in HDL is carried out by a reaction utilizing the action of a chemically modified or unmodified cholesterol ester-hydrolyzing enzyme and the action of a chemically modified or unmodified cholesterol-oxidizing enzyme or of chemically modified or unmodified cholesterol oxidoreductase in the presence of a reagent inhibiting the reaction of lipoproteins other than HDL.

4. The method according to claim 3, wherein said reagent inhibiting the reaction of lipoproteins other than HDL is a combination of a divalent metal salt, and heparin or a salt thereof, phosphotungstic acid or a salt thereof, dextran sulfuric acid or a salt thereof, polyethylene glycol, sulfated cyclodextrin or a salt thereof, sulfated oligosaccharide or a salt thereof, or a mixture thereof.

5. The method according to claim 3, wherein said reagent inhibiting the reaction of lipoproteins other than HDL is an antiapo-B antibody or an antiapo-C antibody.

6. The method according to any of claims 3, 4 or 5, wherein the modified moiety of said chemically modified cholesterol ester-hydrolyzing enzyme, chemically modified cholesterol-oxidizing enzyme, and chemically modified cholesterol oxidoreductase is a group having polyethylene glycol as a main component, a group having polypropylene glycol as a main component, a group having a copolymer of polypropylene glycol and polyethylene glycol, a group having a saccharide in the structure, a sulfopropyl group, or a polyurethane group.

7. The method according to claim 6, wherein said reagent which enables the reaction of cholesterol in LDL is a nonionic, cationic or anionic surfactant, cyclodextrin, a chemically modified or unmodified cholesterol ester-hydrolyzing enzyme capable of acting on LDL, a chemically modified or unmodified cholesterol-oxidizing enzyme capable of acting exclusively on LDL, or chemically modified or unmodified cholesterol oxidoreductase capable of acting on LDL.

8. The method according to claim 1, wherein the reaction for elimination of cholesterol in HDL is carried out by eliminating cholesterol in lipoproteins other than LDL in the presence of a reagent inhibiting only the reaction of LDL.

9. The method according to claim 8, wherein said elimination of cholesterol in lipoproteins other than LDL is followed by the addition of a reagent which enables the reaction of cholesterol in LDL.

10. The method according to claim 9, wherein said reagent inhibiting only the reaction of LDL is a chemically modified or unmodified cholesterol ester-hydrolyzing enzyme capable of inhibiting only the reaction of LDL.

11. The method according to claim 10, wherein the modified moiety of said chemically modified cholesterol esterase is a group having polyethylene glycol as a main component, a group having polypropylene glycol as a main component, a group having a copolymer of polypropylene glycol and polyethylene glycol, a group having a saccharide in the structure, a sulfopropyl group, or a polyurethane group.

12. The method according to any of claims 9, 10 or 11, wherein said reagent which enables the reaction of cholesterol in LDL is a cholesterol ester-hydrolyzing enzyme enabling the reaction of cholesterol in LDL.

13. The method according to any of claims 9, 10 or 11, wherein said reagent which enables the reaction of cholesterol in LDL is a surfactant or a chelating agent.

14. The method according to claim 1, wherein said cholesterol ester-hydrolyzing enzyme, cholesterol-oxidizing enzyme or cholesterol oxidoreductase is an enzyme derived from an animal, a plant or a microorganism, an enzyme obtained by introducing the gene of such an enzyme into other microorganism and subsequent expressing it, or an enzyme obtained by modifying the gene of such an enzyme and subsequent expressing it.

15. The method according to claim 1, wherein the determination of hydrogen peroxide is carried out by converting hydrogen peroxide into a pigment by the action of peroxidase and a chromogen, and determining the pigment.

16. A reagent for the determination of cholesterol in LDL, which contains a reagent inhibiting the reaction of lipoproteins other than HDL and a reagent enabling the reaction of cholesterol in LDL.

17. The reagent according to claim 16, which comprises a reagent inhibiting the reaction of lipoproteins other than HDL and a separate reagent enabling the reaction of cholesterol in LDL.

18. The reagent according to claim 16 or 17, wherein said reagent inhibiting the reaction of lipoproteins other than HDL is a combination of a divalent metal salt, and heparin or a salt thereof, phosphotungstic acid or a salt thereof, dextran sulfuric acid or a salt thereof, polyethylene glycol, sulfated cyclodextrin or a salt thereof, sulfated oligosaccharide or a salt thereof, or a mixture thereof.

19. The reagent according to claim 16 or 17, wherein said reagent inhibiting the reaction of lipoproteins other than HDL is an antiapo-B antibody or an antiapo-C antibody.

20. The reagent according to claim 17, wherein said reagent enabling the reaction of cholesterol in LDL is a nonionic, cationic or anionic surfactant, cyclodextrin, a chemically modified or unmodified cholesterol ester-hydrolyzing enzyme capable of acting on LDL, a chemically modified or unmodified cholesterol-oxidizing enzyme capable of acting exclusively on LDL, or chemically modified or unmodified cholesterol oxidoreductase capable of acting on LDL.

21. A reagent for the determination of cholesterol in LDL, which contains a reagent inhibiting only the reaction of LDL.

22. A reagent for the determination of cholesterol in LDL, which contains a reagent inhibiting only the reaction of LDL and a reagent enabling the reaction of cholesterol in LDL.

23. The reagent according to claim 22, which comprises a reagent inhibiting only the reaction of LDL and a separate reagent enabling the reaction of cholesterol in LDL.

24. The reagent according to any of claims 21, 22 or 23, wherein said reagent inhibiting only the reaction of LDL is a chemically modified or unmodified cholesterol ester-hydrolyzing enzyme capable of inhibiting only the reaction of LDL.

25. The reagent according to claim 24, wherein the modified moiety of said chemically modified cholesterol esterase is a group having polyethylene glycol as a main component, a group having polypropylene glycol as a main component, a group having a copolymer of polypropylene glycol and polyethylene glycol, a group having a saccharide in the structure, a sulfopropyl group, or a polyurethane group.

26. The kit according to claim 22 or 23, wherein said reagent enabling the reaction of cholesterol in LDL is a cholesterol ester-hydrolyzing enzyme enabling the reaction of cholesterol in LDL.

27. The kit according to claim 22 or 23, wherein said reagent enabling the reaction of cholesterol in LDL is a surfactant or a chelating agent.

28. The reagent according to claim 16 or 17, wherein said reagent inhibiting the reaction of lipoproteins other than HDL includes a chemically modified cholesterol ester-hydrolyzing enzyme, a chemically modified cholesterol-oxidizing enzyme, or a chemically modified oxidoreductase which are unreactive to LDL.

29. The reagent according to claim 28, wherein the modified moiety of said chemically modified cholesterol ester-hydrolyzing enzyme, a chemically modified cholesterol-oxidizing enzyme, or a chemically modified oxidoreductase is a group having polyethylene glycol as a main component, a group having polypropylene glycol as a main component, a group having a saccharide in the structure, a sulfopropyl group, or a polyurethane group.

30. The reagent according to any of claims 21, 22 or 23, wherein said reagent inhibiting only the reaction of LDL is a chemically modified cholesterol ester-hydrolyzing enzyme capable of inhibiting only the reaction of LDL.

31. The reagent according to claim 30, wherein the modified moiety of said chemically modified cholesterol ester-hydrolyzing enzyme is a group having polyethylene glycol as a main component, a group having polypropylene glycol as a main component, a group having a copolymer of polypropylene glycol and polyethylene glycol, a group having a saccharide in the structure, a sulfopropyl group, or a polyurethane group.

* * * * *

UNITED STATES PATENT AND TRADEMARK OFFICE
CERTIFICATE OF CORRECTION

PATENT NO. : 5,807,696

DATED : September 15, 1998

INVENTOR(S) : KAZUHITO MIYAUCHI ET AL.   Page 1 of 2

It is certified that error appears in the above-identified patent and that said Letters Patent is hereby corrected as shown below:

COLUMN 3

Line 64, "oxidoreductase)" should read
   --oxidoreductase)],--.
Line 65, "]," should be deleted.

COLUMN 6

Line 9, "cLolesterol-oxidizing" should read --cholesterol-oxidizing--.

COLUMN 8

Line 37, "specifity" should read --specificity--.

COLUMN 9

Line 55, "(cobalt" should read --cobalt--.

COLUMN 14

Line 54, "T).As" should read --T). As--.

COLUMN 17

Line 44, "reaction" should be deleted.
Line 45, "for" should be deleted.

UNITED STATES PATENT AND TRADEMARK OFFICE
CERTIFICATE OF CORRECTION

PATENT NO. : 5,807,696
DATED : September 15, 1998
INVENTOR(S) : KAZUHITO MIYAUCHI ET AL.

It is certified that error appears in the above-identified patent and that said Letters Patent is hereby corrected as shown below:

COLUMN 18

Line 10, "subsequent" should read --subsequently--.
    Line 12, "subsequent" should read --subsequently--.
    Line 35, "claim 17," should read --claim 16 or 17,--.
    Line 66, "kit" should read --reagent--.

COLUMN 19

Line 3, "kit" should read --reagent--.

Signed and Sealed this

Twentieth Day of July, 1999

Attest:

Attesting Officer

Q. TODD DICKINSON

Acting Commissioner of Patents and Trademarks